United States Patent [19]

Obanawa et al.

[11] Patent Number: 4,732,887

[45] Date of Patent: Mar. 22, 1988

[54] COMPOSITE POROUS MATERIAL, PROCESS FOR PRODUCTION AND SEPARATION OF METALLIC ELEMENT

[75] Inventors: Heiichiro Obanawa, Kamakura; Minoru Akiyama, Yokohama, both of Japan

[73] Assignee: Asahi Kasei Kogyo Kabushiki Kaisha, Osaka, Japan

[21] Appl. No.: 784,644

[22] Filed: Oct. 4, 1985

[30] Foreign Application Priority Data

Oct. 12, 1984 [JP] Japan .................. 59-212499
Oct. 12, 1984 [JP] Japan .................. 59-212500

[51] Int. Cl.$^4$ .............................. B01J 20/26
[52] U.S. Cl. ........................ 502/402; 210/679
[58] Field of Search ........................ 502/402

[56] References Cited

U.S. PATENT DOCUMENTS

| | | | |
|---|---|---|---|
| 4,049,496 | 9/1977 | Henry | 195/66 R |
| 4,140,653 | 2/1979 | Imura et al. | 502/402 X |
| 4,335,017 | 6/1982 | Miles et al. | 502/402 X |
| 4,336,161 | 6/1982 | Rosevear et al. | 502/402 X |
| 4,386,006 | 5/1938 | Harrington | 502/402 X |

*Primary Examiner*—Patrick P. Garvin
*Attorney, Agent, or Firm*—Birch, Stewart, Kolasch & Birch

[57] ABSTRACT

A composite porous material comprising a particulate inorganic porous material and, contained in the pores of the material, an organic resin having a micro-void. The composite porous material has a surface area larger than that of the inorganic porous material. The composite porous material has a high dimensional stability comparable to that of an inorganic porous material while exhibiting a high separating and adsorbing capacity comparable to that of the conventional ion exchange resin or chelate resin. Therefore, it can advantageously be used as an adsorbent for various compounds or ions as well as a packing material for gas or liquid chromatography.

16 Claims, No Drawings

COMPOSITE POROUS MATERIAL, PROCESS FOR PRODUCTION AND SEPARATION OF METALLIC ELEMENT

This invention relates to a composite porous material, a process for producing the same, and a process for the separation of a metallic element. More particularly, the present invention is concerned with a composite porous material comprising a particulate inorganic porous material and, contained in the pores thereof, an organic resin having a micro-void, and a process for producing the composite porous material. It is also concerned with a process for the separation of a metallic element from a solution using the composite porous material.

Functional resins such as an ion exchange resin and a chelate resin, and functional polymer gels such as a crosslinked dextran and a crosslinked polystyrene, which have a high separating and adsorbing capacity for a substance, are widely used in separation and adsorption processes, particularly, in partition chromatography, adsorption chromatography, ion exchange chromatography, gel chromatography and the like. Known resins and polymer gels utilized for such purposes, however, are not sufficient in mechanical strength and dimensional stability of particles. Accordingly, due to the insufficient mechanical strength and dimensional stability of particles, use of such a resin or gel, for example, as a packing material for liquid chromatography is possible only under restricted conditions. That is, the height of the column, packing density of the resin particles, developing pressure, constructions of the pump and centrifuge and the like undergo severe restrictions. Because of these restrictions, it is not possible to conduct separation or adsorption of a metal ion or the like by the use of such a resin or gel in a desirable manner. Illustratively stated, in a separation process, the use of such a resin or gel tends to cause the separation time to disadvantageously increase and the yield and separation efficiency to disadvantageously decrease. In an adsorption process, the use of such a resin or gel tends to cause the adsorption time, the number of operation cycles and the needed adsorbent amount to disadvantageously increase. Further, dimensional changes due to swelling of the resin or gel by the developer cause the packing density of the packing material at the development to change, so that when several kinds of developers are to be passed through the column packed with the resin or gel, the packing density becomes unstable, whereby stable development cannot be attained by the use of the resin or gel.

These drawbacks are serious problems in utilizing such a resin or gel in a separation process, an adsorption process, and other various processes in industries. Therefore, efforts have been made in the art to solve the technical problems that the high separating and adsorbing capacity of the resin or gel which cannot be sufficiently exhibited due to the insufficient mechanical strength and dimensional stability of the resin or gel. As is apparent from the foregoing, there is a strong demand in the art for a packing material having a high mechanical strength and dimensional stability as well as a high separating and adsorbing capacity.

In order to obviate the above-mentioned problems of insufficient mechanical strength and dimensional stability, there has been proposed a composite material formed by coating a polymer over the exterior and interior surfaces of inorganic porous particles thereby, to take advantage of the excellence in such properties of the inorganic material. In this connection, reference may be made to, for example, U.S. Pat. No. 4,140,653. Likewise, there has been proposed a composite material comprising inorganic porous particles having a stationary phase coupled to the surfaces thereof through a coupling agent. See U.S. Pat. No. 4,049,496. These composite materials are, however, accompanied by the following drawback. In these composite materials, the layer of the coated resin or stationary phase is naturally very thin and, therefore, the volume amount thereof is extremely small as compared with the volume of the composite material. For this reason, the amounts of adsorption and separation of a substance per unit weight of such composite materials are extremely small. In order to atain adsorption and separation of a substance in a large amount as attained with a porous resin, a very large amount of the composite material is required. Accordingly, such composite materials have been practically employed only in specific fields in which adsorption and separation of a substance in a small amount is sufficient. In the case of the resin-coated composite material mentioned above, when the increased amount of resin is coated over the surfaces of the inorganic porous particles, the composite material is defective in that chemical species relating to the adsorption or separation diffuse into the coated resin at an extremely low rate, that the sites at which the adsorption or separation occurs are present only on the surfaces of the resin, and that hence it takes a relatively long time to begin to exhibit its adsorbing or separating capability. Further, when the amount of resin coated over the surfaces of the inorganic porous particle is too much, the micropores of the particles are closed whereby the adsorbing and separating capacity of the composite material is greatly reduced.

The above-mentioned conventional two types of composite materials comprise a large proportion of an inorganic porous particle and only a small proportion of a resin, so that the properties of the conventional composite materials are mainly affected by the properties of the inorganic porous particle. Therefore, such known composite materials have high mechanical strength and dimensional stability but cannot exhibit adsorption and separation performances comparable to those of the conventional porous resins.

With a view to obtaining a composite porous material having a high mechanical strength and dimensional stability while exhibiting excellent performance with respect to adsorption and separation, the inventors have made extensive and intensive studies. As a result, the inventors have unexpectedly found that a composite material suitable for the purpose can be obtained by incorporating an organic resin having a micro-void in the pores of a particulate inorganic porous material. Based on such a novel finding, the present invention has been completed.

It is therefore an object of the present invention to provide a composite porous material having a high mechanical strength and dimensional stability while exhibiting a high adsorbing and separating capacity comparable to those of the conventional porous resins.

It is another object of the present invention to provide a process for producing such a composite porous material of the kind mentioned above.

It is a further object of the present invention to provide a process for the separation of a metallic element from a solution containing the same by the use of the composite porous material.

The foregoing and other objects, features and advantages of the present invention will be apparent to those skilled in the art from the following detailed description and appended claims.

According to one aspect of the present invention, there is provided a composite porous material comprising a particulate inorganic porous material and, contained in the pores of said inorganic porous material, an organic resin having micro-voids, said composite porous material having a surface area greater than that of said inorganic porous material. In the composite porous material of the present invention, the resin having micro-voids is disposed in the pores of the inorganic porous material so that it fills the pores partially or completely. Further, as compared with the conventional coating type composite material in which the resins having no micro-void is present only on the surface portions of the particulate inorganic porous material, the composite material of the present invention has a large amount of an organic resin per unit weight of the inorganic porous material and has micro-voids in the resin, whereby the sites at which adsorption or separation occurs are present not only on the surface of the resin but also in the interior portions throughout the resin.

In the composite porous material of the present invention, the micro-voids of the resin have a specific function that is different from that of the pores of the conventional ion exchange resin. The reason is as follows. In the case of the conventional ion exchange resins, the resin is swollen, upon contact with a solution containing ions the to be exchanged, by the permeation of the solution into the pores, whereby a sufficient passage is established for the ions to reach the ion exchange groups on the resin more easily. On the other hand, in the composite porous material of the present invention, an organic resin, for example, an ion exchange resin, is contained in the pores of the particulate inorganic porous material with high rigidity, so that swelling of the resin by contact with a solution containing ions is inhibited by the walls of pores of the inorganic porous particles. However, the composite porous material of the present invention is able to exhibit its excellent functions because the resin has micro-voids of appropriate volume, diameter and diameter distribution. The micro-voids are not only useful for permeation of the solution into the composite porous material but also provides large number of reaction sites.

In the composite porous material of the present invention, the organic resin contained in the composite porous material has micro-voids in a quantity sufficient to render the total surface area of the composite porous material greater than that of the inorganic porous material contained therein.

The properties of the composite porous material of the present invention depend on not only the particle diameter, surface area, pore characteristics (pore volume, average pore diameter and pore diameter distribution) and material of the particulate inorganic porous material but also the micro-void characteristics (i.e., micro-void volume, average micro-void diameter and micro-void diameter distribution) and the kind of organic resin as well as the ratio of the organic resin to the composite porous material.

With respect to the pore characteristics of the particulate inorganic porous material, they may be analyzed by heating the composite porous material, for example, at 700° to 800° C. until all of the resin is burnt out to obtain an organic resin-free inorganic porous material, and subjecting the thus obtained inorganic porous material to measurement by means of a mercury porosimeter (Autopore 9200, manufactured and sold by Shimadzu Corporation, Japan), thereby to determine the pore volume and average pore diameter of the material. Using this data, the surface area may be calculated according to a postulated cylindrical pore model, as explained later. On the other hand, with respect to the properties of the pores of the composite porous material, they may be determined by means of a mercury porosimeter without subjecting the composite porous material to pretreatment. The surface area may be calculated in the same manner as in the case of the inorganic porous material.

The properties of the micro-voids of the organic resin may be determined from the data on the pores, weights and specific gravities of the composite porous material and particulate inorganic porous material in accordance with the method as will be described hereinafter.

As the particulate inorganic porous material, there may be employed particulate porous ceramics containing a metallic oxide as a main component. Specific examples of the particulate porous ceramics containing a metallic oxide include a particulate porous silica, a particulate porous alumina, a particulate porous silica-alumina, a particulate porous titania and a particulate porous zirconia. They also include a particulate porous glass, a particulate porous chamotte and a particulate porous porcelain. They may be easily obtained by customary methods. (See, for example, "Technical Compilation of Ceramic Materials " page 224, 1979, Sangyo Gijutsu Center, Japan.) Of them, particulate porous silica is most preferred, because of easy production of particulate porous silica in a substantially spherical form, and narrow diameter distribution and acid-inertness of the produced particulate porous silica. Particulate porous silica useful in the present invention may be made by the following method. An inorganic salt such as sodium chloride is added to a silica sol or a water glass, the resulting silica sol or water glass is spayed by means of, for example, a spray dryer to obtain inorganic salt-containing silica gel particles as an intermediate, and the intermediate is calcined at, for example, 500° C. or more, followed by desalting. In place of the above intermediate, there may also be employed a product obtained by incorporating an inorganic salt in a silica gel which has been formed by means of a spray dryer. In these processes, desired pore diameters and a narrow distribution of pore diameters can be attained by selecting the kind of inorganic salts to be employed and controlling the amount of the salt and the temperature for calcination. The thus obtained particulate porous silica has such a high purity (98% or more) that it can exhibit an excellent chemical resistance to aqueous solutions, especially to an acid solution.

The particle shape of the particulate inorganic porous material of the composite porous material of the present invention is not critical. In general, however, it is preferably spherical or nearly spherical. Suitable particle diameter of the particulate inorganic porous material depends on its use. However, it is preferably in the range of from 10 $\mu$m to 1 mm, especially from 20 $\mu$m to 500 $\mu$m.

The average particle diameter of the particulate inorganic porous material may be measured using an enlarged photograph obtained by means of an optical microscope (Model BH-2, manufactured and sold by Olympus Co., Japan). The diameter is calculated as follows. On the obtained photograph, 100 particle images are arbitrarily selected and the maximum diameter of each particle in a certain direction, e.g., the direction along a side edge of the photograph, is measured with a scale. Then, a mean value is calculated from the thus obtained diameter data to give the average particle diameter of the particulate inorganic porous material.

The terminology "pore volume ratio" used herein is intended to mean a ratio of the volume of pores contained in the particulate inorganic porous material to the apparent volume of said porous material. Although it is possible to employ a particulate inorganic porous material having a pore volume ratio of from 0.01 to 0.99, the ratio is preferably in the range of from 0.3 to 0.9, more preferably from 0.40 to 0.85. The pore volume ratio ($\alpha$) is represented by the following formula:

$$\alpha = 1 - \frac{\text{apparent specific gravity}}{\text{true specific gravity}}.$$

The apparent and true specific gravities may be determined by means of a mercury porosimeter or a pycnometer using mercury and helium. When the ratio is less than 0.3, the amount of the organic resin having micro-voids and contained in the inorganic porous material is too small for the purpose, thereby causing the adsorbing and separating capacities of the composite porous material to be disadvantageously lower. When the ratio is more than 0.9, the mechanical strength of the composite porous material is too low for the purpose, thereby causing its handling to be difficult.

The average pore diameter of the particulate inorganic porous material may be measured by means of a mercury porosimeter. The terminology "pore" used herein is intended to mean a pore having a pore diameter of not less than 3.7 nm, which is the minimum value that can be measured by means of the mercury porosimeter. The average pore diameter of the particulate inorganic porous material is not especially limited. However, it is preferably in the range of from 20 to 2000 nm, more preferably from 50 to 1500 nm.

The surface area (S) of the particulate inorganic porous material can be represented by the formula:

$$S = \frac{4V}{D}$$

wherein V is the pore volume and D is the average pore diameter. The above formula may be derived from the following two formulas which are derived according to a postulated cylindrical pore model:

$$S = \pi DL \text{ and}$$

$$V = \frac{\pi}{4} D^2 \cdot L$$

wherein S, V and D are as defined above, and L is the length of the postulated cylindrical pore. If S is determined with respect to a unit weight, i.e. 1 gram, of the particulate inorganic porous material, the obtained value represents a specific surface area of the material. It is preferred that the specific surface area of the inorganic porous material be in the range of from 0.1 to 1000 $m^2/g$, especially from 0.4 to 800 $m^2/g$.

The surface area of the composite porous material of the present invention may be determined in substantially the same manner as in the case of the inorganic porous material mentioned above.

In the composite porous material of the present invention, it is essential that the surface area of the composite porous material be greater than the particulate inorganic porous material of conventional composite porous materials. Accordingly, the following relationship is to be satisfied:

$$Wc \cdot Sc > Wi \cdot Si$$

wherein Wc and Wi are the weights in terms of grams of the composite porous material and inorganic porous material, respectively, and Sc and Si are the specific surface areas in terms of $m^2/g$ of the composite porous material and inorganic porous material, respectively. If a composite porous material does not satisfy the above relationship, it is expected that the amount of the contained organic resin is too small or that the surface area of the micro-void of the organic resin is too small. Such a composite porous material not satisfying the above relationship is outside the scope of the present invention.

The organic resin having micro-voids that are contained in the composite porous material of the present invention has an average micro-void diameter preferably not greater than 90%, more preferably not greater than 50%, of the average pore diameter of the particulate inorganic porous material. The suitable average micro-void diameter of the resin varies depending on the use of the ultimate composite material and the average pore diameter of the inorganic porous material. But, in general, it is preferably not greater than 800 nm, more preferably not larger than 100 nm. There is no critical lower limit for the average micro-void diameter. It is, however, preferred that the diameter be not less than 10 nm to ensure prompt ion exchange or prompt chemical treatment for introducing a functional group into the resin.

The average micro-void diameter of the organic resin may be determined from a curve showing the relationship between the pore diameter and pore volume of the composite porous material as obtained by the use of a mercury porosimeter, with reference to the micro-void volume ratio which is determined according to a method mentioned below. Such a curve is also referred to as "pore diameter distribution curve". When the organic resin completely fills all of the pores of the inorganic porous material, the obtained pore diameter distribution curve gives a hill-like curve. In this case, the average pore diameter of the composite porous material is equal to the average micro-void diameter of the organic resin. On the other hand, when the organic resin does not completely fill all of the pores of the inorganic porous material, the obtained pore diameter distribution curve gives a curve composed of two hills. One of the hills is assigned to the micro void of the organic resin, and the other of the hills is assigned to the remaining pores of the inorganic porous material. By previously measuring the micro-void ratio, it is possible to judge which of the hills gives a pore volume corresponding to the micro-void ratio, namely, which of the hills gives the micro-void volume of the resin. Consequently, from that hill, the average micro-void diameter of the resin can be determined.

The terminology "micro-void volume ratio" used herein is intended to mean a ratio of the volume of the micro-voids contained in the organic resin to the volume of the organic resin including the micro-voids. The micro-void volume ratio ($\gamma$) is represented by the following formula:

$$\gamma = 1 - \frac{\frac{Wr}{\rho r}}{Vt \cdot \alpha}$$

wherein Wr is the weight of the organic resin, $\rho r$ is the true specific gravity of the organic resin, Vt is the apparent volume of the inorganic porous material and $\alpha$ is the pore volume ratio of the inorganic porous material. The above relationship is valid where the organic resin completely fills all of the pores of the inorganic porous material. In the case where the organic resin does not completely fill all of the pores of the inorganic porous material, the micro-void volume ratio is represented by the following formula:

$$\gamma = 1 - \frac{\frac{Wr}{\rho r}}{Vt \cdot \alpha \cdot f}$$

wherein Wr, $\rho r$, Vt and $\alpha$ are as defined above, and f is a ratio of the apparent volume of organic resin (Vs) to the apparent volume of inorganic porous material (Vt). The values of Vt and $\alpha$ may be determined by means of a mercury porosimeter. The values of $\rho r$ and Vs may be determined by means of a mercury porosimeter using a sample obtained by treating the composite porous material with, for example, a hydrofluoric acid to remove silica or a heated sulfuric acid solution to remove alumina. The micro-void volume ratio of the organic resin is preferably in the range of from 0.05 to 0.95, more preferably from 0.20 to 0.95, most preferably from 0.40 to 0.95.

The amount ($\beta$) of the organic resin contained in the pores of the inorganic porous material is represented by the following formula:

$$\beta = 1 - \frac{Wi}{Wc}$$

wherein Wi is the weight of the inorganic porous material and Wc is the weight of the composite porous material. Preferably, $\beta$ is in the range of from 0.05 to 0.95, more preferably from 0.20 to 0.80. If $\beta$ is less than 0.05, the amount of the organic resin contained in the composite porous material is so small that the separating and adsorbing capacities of the composite porous material are greatly decreased. When $\beta$ is larger than 0.95, the organic resin is disadvantageously present out of the pores of the inorganic porous particle and/or the micro-void volume ratio is too small, thereby causing the mechanical strength or the separating and adsorbing efficiency of the composite porous material to decrease.

The values of Wi and Wc are measured as follows. From a composite porous material, two specimens having the same weight are prepared. One is heated, for example, at 800° C. for 30 minutes to remove the organic resin, and weighed to give a value of Wi. The other is weighed without any treatment to give a value of Wc.

A portion of the organic resin may be present on the outer surface of the inorganic porous material. The terminology "outer surface" used herein is intended to mean all the surfaces of the inorganic porous particle, exclusive of the inner surfaces defining the micro-voids. That is, the outer surface is the surface confronting the outer space of the inorganic porous material.

In the present invention, the amount of the resin present on the outer surface of the inorganic porous material is referred to as an "outer resin volume ratio ($\mu$)" defined by the following formula:

$$\mu = \frac{Y - X}{X}$$

wherein X is the apparent volume of the inorganic porous material and Y is the apparent volume of the composite porous material. Each of X and Y can be determined using a mercury porosimeter as follows. First, a sample is put in a container having a predetermined inner volume. Second, the container is deaerated by a vacuum pump and mercury is introduced into the container in a non-pressurized state. Third, the apparent volume of the sample is calculated by subtracting the volume of the introduced mercury from the inner volume of the container. When the sample is an inorganic porous material, X is given. On the other hand, when the sample is a composite porous material, Y is given. In the composite porous material of the present invention, the outer resin volume ratio is preferably not larger than 0.1, more preferably not larger than 0.01. When a composite porous material having an outer resin volume ratio as high as more than 0.1 is used as a packing material for liquid chromatography, a part of the resin present on the outer surface of the inorganic porous material tends to be detached from the outer surface by the friction between the composite porous materials, and the detached resin clogs the filter, thereby causing the pressure loss to increase. Also it may occur that the thus detached resin stays among the packing materials, thereby causing the separating and adsorbing capacities of the packing material to decrease with the repetition development. Further, the resin present on the outer surface of the inorganic porous material may be detached therefrom, for example, during the transportation of a slurry of the composite porous material by the use of a pump, or during the mixing of the composite porous material by the use of a mixer.

In the present invention, the matrix resin of the organic resin having micro-voids to be contained in the pores of the particulate inorganic porous material is not critical with respect to the chemical properties such as the components and molecular structure of the resin, and may be selected from a variety of resins. The abovementioned matrix resin may be selected from the group consisting of natural polymers such as polysaccharides (for example, dextran, agarose and cellulose), polypeptides, proteins and the like, and synthetic polymers such as polystyrene, polyvinyl alcohol, polyacrylonitrile, polyvinyl chloride, polybutadiene, polyethylene terephthalate, 6,6-nylon, polyphenylene sulfide, poly(2,6-xylenol), polyether sulfone, polyethylene, polypropylene, polyacrylic acid, polyvinyl acetate, a copolymer of acrylonitrile and styrene, a copolymer of styrene and butadiene, a copolymer of styrene and vinylbenzyl chloride, a copolymer of vinyl acetate and vinyl chloride, a copolymer of acrylic acid and styrene, phenol resin, melamine resin, epoxy resin, alkyd resin, and the like. In the present invention, generally, the resins are crosslinked. The reason for the preference for the crosslinked resins as compared to linear resins is that in the case of a crosslinked resin, the micro-voids of the resin will be maintained for a prolonged period of time and the detachment of the resin from the pores of the inorganic porous material will be prevented due to the fixed geometrical structure of the resin. The suitable crosslinking degree of such a crosslinked resin may vary depending on the use of the ultimate composite material. However, the amount of the crosslinking units contained in the resin is generally 90% or less, preferably in the range of from 0.1 to 80%, more preferably in the range of from 1 to 50%, based on the total weight of the resin.

It is often preferred that the matrix resin of the organic resin having micro-voids to be contained in the pores of the particulate inorganic porous material have a functional group. Hence, an ion exchange resin, a chelate resin having a chelate ligand and a redox resin having a hydroquinone group, thiol group or the like are useful to constitute, together with the particulate inorganic porous material, the composite porous material of the present invention.

The ion exchange resin to be employed in the present invention includes a cation exchange resin, an anion exchange resin and a resin having both cation exchange and anion exchange capabilities.

As the suitable cation exchange resin, there may be mentioned, for example, those having a sulfonic acid group, a carboxyl group, a phosphoric acid group or the like. These resins generally have a three-dimensional structure, and may be polymerized from a monomer such as vinylbenzenesulfonic acid, vinylbenzoic acid, acrylic acid, methacrylic acid and the like.

As the suitable anion exchange resin, there may be mentioned, for example, those having a primary, secondary or tertiary amine such as polystyrene or polyacrylamide having in its side chain a functional group represented by the formula:

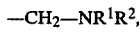

—CH$_2$—NR$^1$R$^2$, wherein R$^1$ and R$^2$ each independently stand for a straight-chain alkyl group having 1 to 5 carbon atoms; those having a quaternary ammonium group represented by the formula:

—CH$_2$—N$^+$R$^1$R$^2$R$^3$X—, wherein
R$^1$ and R$^2$ are as defined above, R$^3$ stands for a straight-chain alkyl group having 1 to 5 carbon atoms, and X$^-$ stands for a monovalent inorganic anion such as Cl$^-$, Br$^-$, I$^-$, NO$_3^-$ and ClO$_4^-$ or a chemical equivalent of a multivalent inorganic anion such as $\frac{1}{2}$ SO$_4^{--}$ and $\frac{1}{3}$ PO$_4^{---}$;
those polymerized from a monomer such as vinylpyridine, vinylimidazole and the like which have a basic nitrogen-containing heterocyclic ring as a functional group; and the like. Suitable heterocyclic rings include not only those of pyridine and imidazole but also those of pyrazole, thiazole, triazole, carbazole, benzimidazole, indole and the like.

As the suitable chelate resin to be employed in the present invention, there may be mentioned, for example, those having a chelate group comprising a plurality of identical or different functional groups such as an alcohol, a phenol, a carboxyalic acid, an aldehyde, an amide, an ester, an oxide, a primary amine, a secondary amine, a tertiary amine, a thioether, a thiophenol, an arylphosphine and an arylarsine. Moreover, as the specific examples of the suitable chelate resin, there may be mentioned a polymer having a hydoxyl group, such as polyvinyl alcohol; a polymer having a ketonic carbonyl group originating from such monomers as vinyl methyl ketone and methacryloylacetone, a polymer having a hydroxyl group and a carboxyl group, such as salicylic acid-formaldehyde resin; a polymer having a carboxyl group such as polyacrylic acid, polymethacrylic acid, polyitaconic acid and thiophene maleate; a polymer having an iminodiacetic group; a polymer having an amino group, an oxime group or an azo group; a polymer having a thioalcohol group or a thiophenol group; a polymer having a thioketone group, a dithiolate group, a thioamide group or a thiourea group; a polymer having a primary, secondary or tertiary alkyl phosphine group or an arylphosphine group; a polymer having a catechol group, and the like. As preferred chelate resins, there may be mentioned a polymer having in its molecule a structure of a polyaminocarboxylic acid, various oximes, oxine, or catechol.

As an example of the suitable polyaminocarboxylic acid, there may be mentioned a compound represented by the formula (I):

wherein R$^4$, R$^5$ and R$^6$ each independently represent a hydrogen atom or —CH$_2$COOR$^8$ in which R$^8$ represents a hydrogen atom, an alkali metal ion or a hydrocarbon residue having from 1 to 4 carbon atoms; A$^1$, A$^2$ and A$^3$ each independently represent

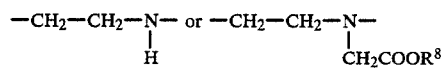

—CH$_2$—CH$_2$—N— or —CH$_2$—CH$_2$—N—
               |                        |
               H                   CH$_2$COOR$^8$ and i, j and k each independently represent an integer of from 0 to 3, provided that a compound represented by formula (I) contains at least one —CH$_2$COOR$_8$ therein.

As such polyaminocarboxylic acids, there may be mentioned, specifically, a polyaminocarboxylic acid having a nitrogen atom such as iminodiacetic acid, derivatives thereof such as N-methyliminodiacetic acid, N-cyclohexyliminodiacetic acid, N-phenyliminodiacetic acid and the like, and nitrilotriacetic acid; a polyaminocarboxylic acid having two nitrogen atoms such as ethylenediamine-N,N,N',N'-tetraacetic acid, derivatives thereof such as 1,2-propylenediamine-N,N,N',N'-tetraacetic acid, 1-phenylethylenediaminetetraacetic-N,N,N',N'-acid, cyclohexyldiamine-N,N,N',N'-tetraacetic acid and the like; a polyaminocarboxylic acid having three or more nitrogen atoms such as diethylenetriamine-N,N,N',N'',N''-pentaacetic acid, diethylenetriamine-N,N,N'',N'''-tetraacetic acid of the formula,

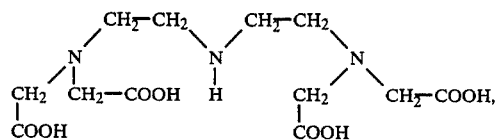

diethylenetriamine-N,N,N',N"-tetraacetic acid of the formula,

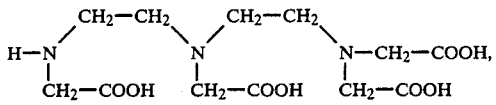

derivatives thereof, triethylenetetramine-N,N,N',N",N''',N''''-hexaacetic acid, polyethyleneimine, and polyethyleneimine having an acetic acid group introduced therein. Further, the specific examples of the suitable polyaminocarboxylic acids include N-hydroxyethylenediamine-N,N',N'-triacetic acid, 1,3-diaminopropane-N,N,N',N'-tetraacetic acid, 1,4-diaminobutane-N,N,N',N'-tetraacetic acid, and the like. Of them, more preferable polyaminocarboxylic acids may be iminodiacetic acid, ethylenediaminetetraacetic acid, diethylenetriamine-N,N,N",N"-tetraacetic acid, diethylenetriamine-N,N',N",N"-tetraacetic acid and derivatives thereof.

These chelate compounds are contained in chelate resins in the form of a radical produced through removal of one or more hydrogen atoms from the compound at any position.

The kind of the resin for introducing such a chelate group to be contained in the composite porous material is not critical. For example, there may be mentioned a copolymer of styrene and divinylbenzene into which various substituents have been introduced.

The chelate resin to be used in the present invention has the typical structure which has repeating units as represented by formulas (II) and (III). These chelate resins may be produced by, for example, a process in which a copolymer of chloromethylstyrene and divinylbenzene is reacted with an iminodicarboxylic acid ethyl ester [formula (II)], a process in which a copolymer of (1,2-dibromoethyl)styrene and divinylbenzene is reacted with iminodiacetic acid [formula (III)], a process in which a copolymer of chloromethylstyrene and divinylbenzene is reacted with diethylenetriamine and then with chloroacetic acid [formula (II)] and a process in which a copolymer of p-[di(aminoethyl)aminoethyl]styrene and divinylbenzene is reacted with chloroacetic acid [formula (II)].

Formula (II)

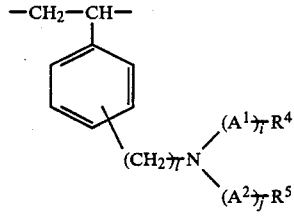

wherein
$A^1$ and $A^2$ each independently represent

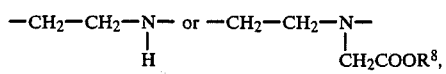

$R^4$ and $R^5$ each independently represent —H— or —CH$_2$COOR$^8$, i and j each independently represent an integer of 0 to 3, l represents an integer of 1 to 3,
$R^8$ represents H, an alkali metal ion or a hydrocarbon residue having 1 to 4 carbon atoms, provided that at least one of $A^1$, $A^2$, $R^4$ and $R^5$ is or contains —CH$_2$COOR$^8$.

Formula (III)

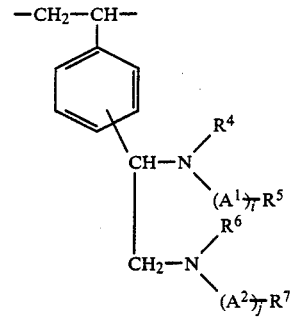

wherein
$A^1$ and $A^2$ each independently represent

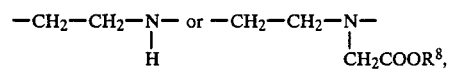

$R^4$, $R^5$, $R^6$ and $R^7$ each independently represent —H or —CH$_2$COOR$^8$,
i and j each independently represent an integer of 0 to 3,
$R^8$ represents a hydrogen atom, an alkali metal ion or a hydrocarbon residue having 1 to 4 carbon atoms, provided that at least one of $A^1$, $A^2$ and $R^4$ to $R^7$ is or contains —CH$_2$COOR$^8$.

As a specific example of a chelate resin containing an oxime, there may be mentioned a resin obtained through a process in which a polymer having a carbonyl group is reacted with hydroxylamine. The reaction may be effected in the pores of the inorganic porous material.

As a specific example of a chelate resin containing an oxine structure, there may be mentioned a polymer obtained by an addition condensation reaction of oxine and formalin. Alternatively, a chelate resin containing an oxine structure may be obtained by reacting a polymer having a formyl group or a hydroxyl group with oxine. The reaction may be effected in the pores of the inorganic porous material.

A chelate resin containing a catechol group may be one having a group represented by the following formula (IV):

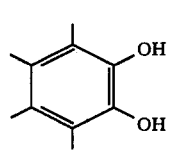

wherein three of the four hydrogen atoms bonded to the benzene ring may be replaced by any substituent.

The structure of the polymer containing a catechol group to be employed in the present invention is not critical, but some preferable examples can be mentioned. The first example is a polymer having a repeating unit represented by the following formula (V):

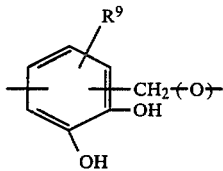

wherein the presence of 0 in the parentheses is optional, and $R^9$ represents a hydrogen atom or a hydrocarbon residue having 1 to 8 carbon atoms.

Such a polymer having the above-mentioned repeating unit may be produced by a polyaddition condensation reaction of catechol or a modified catechol as mentioned above with formaldehyde. Further, according to need, in the above-mentioned polyaddition condensation reaction, there may be added hydroxybenzenes such as phenol, resorcinol and p-chlorophenol, aminobenzenes such as aniline, p-phenylenediamine and o-phenylenediamine, and phenyl ethers such as anisole and diphenyl ether.

The second example of the polymer containing a catechol group is a polymer having a repeating unit represented by the following formula (VI):

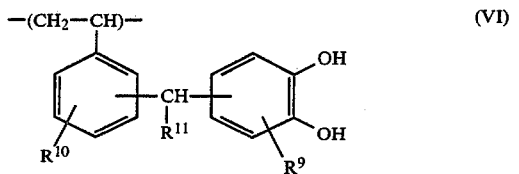

wherein
$R^9$ and $R^{10}$ independently represent a hydrogen atom or a hydrocarbon residue having 1 to 8 carbon atoms,
$R^{11}$ represents a hydrogen atom, a hydroxyl group, a hydrocarbon residue having 1 to 8 carbon atoms or a catechol group.

Such a polymer having the above-mentioned repeating unit may be produced by an addition of a catechol to a three-dimensional crosslinked copolymer of a styrene derivative having a formyl group or a hydroxyl group or by a dehydration condensation of a catechol and such a three-dimensional crosslinked copolymer. In the case of a repeating unit represented by formula (V), for example, a three-dimensional crosslinked repeating unit as represented by formula (VII) is formed by reacting one mole of a catechol with two or more moles of formaldehyde thereby to give a three-dimensional crosslinked polymer.

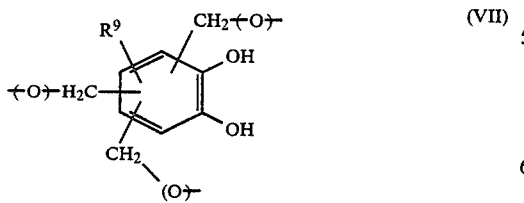

wherein $R^9$ is as defined above.

The organic resin in a crosslinked form may be produced by the use of a crosslinking agent which may be a bifunctional or multifunctional monomer thereby to give a three-dimensional stucture. As such crosslinking agent to be used with a monomer having a vinyl group, there may be mentioned, for example, divinylbenzene, divinyltoluene, divinylxylene, divinylethylbenzene, trivinylbenzene, divinyldiphenyl, divinyldiphenylmethane, divinyldibenzyl, divinyl phenyl ether, divinyldiphenyl sulfide, divinyldiphenylamine, divinyl sulfone, divinyl ketone, divinylpyridine, diallyl phthalate, diallyl maleate, diallyl fumarate, diallyl succinate, diallyl oxalate, diallyl adipate, diallyl sebacate, diallylamine, triallylamine, N,N'-ethylenediacrylamide, N,N'-methylenediacrylamide, N,N'-methylenedimethacrylamide, ethylene glycol dimethacrylate, ethylene glycol diacrylate, 1,3-butylene glycol diacrylate, triallyl isocyanurate, triallyl citrate, triallyl trimellitate, triallyl cyanurate and the like.

According to another aspect of the present invention, there is provided a process for producing a composite porous material, which comprises contacting a particulate inorganic porous material with a homogeneous liquid mixture selected from the group consisting of a mixture of a polymerizable monomer or oligomer, a crosslinking agent and a diluent and a mixture of a polymer, a crosslinking agent and a diluent to introduce said homogeneous liquid mixture into the pores of said particulate inorganic porous material, heating or exposing to actinic rays the mixture to produce an intermediate product comprising said inorganic porous material and, disposed in the pores of said inorganic porous material, a crosslinked polymer containing the diluent and removing the diluent from said intermediate product.

In the present process, an inorganic porous material is contacted with a homogeneous liquid mixture. As the homogeneous liquid mixture, there is employed a mixture of a polymerizable monomer or oligomer, a crosslinking agent and a diluent, or a mixture of a polymer, a crosslinking agent and a diluent. By the contact of the inorganic porous material with the homogeneous liquid mixture, there is obtained an inorganic porous material having in its pores the homogeneous liquid mixture.

As a monomer to be introduced with a crosslinking agent into the pores of the particulate porous materials to form a crosslinked resin, a monomer having a vinyl group may preferably be used. As examples of such a monomer, there may be mentioned hydrocarbons such as styrene, methylstyrene, diphenylethylene, ethylstyrene, dimethylstyrene, vinylnaphthalene, vinylphenanthrene, vinylmesitylene, 3,4,6- trimethylstyrene, 1-vinyl-2-ethylacetylene, butadiene, isoprene and the like; styrene derivatives such as chlorostyrene, methoxystyrene, bromostyrene, cyanostyrene, formylstyrene, fluorostyrene, dichlorostyrene, N,N-dimethylaminostyrene, nitrostyrene, chloromethylstyrene, trifluoromethylstyrene, aminostyrene and the like; vinyl sulfide derivatives such as methyl vinyl sulfide, phenyl vinyl sulfide and the like; acrylonitrile and acrylonitrile derivatives such as methacrylonitrile, α-acetoxyacrylonitrile and the like; acrylic and methacrylic acids; acrylic esters such as methyl acrylate, lauryl acrylate, chloromethyl acrylate, ethyl acetoxyacrylate and the like; methacrylic esters such as cyclohexyl methacrylate, dimethylaminoethyl methacrylate, glycidyl methacrylate, tetrahydrofurfuryl methacrylate, hydroxyethyl methacrylate and the like; diethyl maleate and fumarate;vinylketones such as methyl vinyl ketone, ethyl isopropenyl ketone and the like; vinylidene compounds such as vinylidene chloride, vinylidene bromide, vinylidene cyanide and the like; acrylamide and derirvatives thereof such as methacrylamide, N-butoxymethylacrylamide, N-phenylacrylamide, diacetonacrylamide, N,N-dimethylaminoethylacrylamide and the like; vinyl esters of a fatty acid such as vinyl acetate, vinyl butyrate, vinyl caprate and the like; derivatives of a thiofatty acid such as phenyl thiomethacrylate, methyl thioacrylate, vinyl thioacetate and the like; nitrogen-containing heterocyclic compounds such as 2-vinylpyrrole, N-vinylpyrrole, N-vinylpyrrolidone, N-vinylsuccinimide, N-vinylphthalimide, N-vinylcarbazole, N-vinylindole, 2-vinylimidazole, 5-vinylimidazole, 1-vinyl-2-methylimidazole, 1-vinyl-2-hydroxymethylimidazole, 5-vinylpyrazole, 3-methyl-5-vinylpyrazole, 3-vinylpyrazoline, vinylbenzoxazole, 3-phenyl-5-vinyl-2-isoxazoline, N-vinyloxazolidone, 2-vinylthiazole, 2-vinyl-4-methylthiazole, 2-vinyl-4-phenylthiazole, 2-vinyl4,5-dimethylthiazole, 2-vinylbenzothiazole, 1-vinyltetrazole, 2-vinyltetrazole, 2-vinylpyridine, 4-vinylpyridine, 2-N, N-dimethylamino-4-vinylpyridine, 2-vinyl-4,6-dimethyltriazine, 2-vinyl-4,6-diphenyltriazine, isopropenyltriazine, vinylquinoline and the like; and other heterocyclic compounds such as vinylfuran, 2-vinylbenzofuran, vinylthiophene and the like. Of course, a plurality of different monomers may be employed to form a copolymer within the pores of the inorganic porous material.

In place of the above-mentioned monomer, an oligomer or a polymer may be employed to form, together with a crosslinking agent and a diluent, a homogeneous liquid mixture. The oligomer to be employed in the present invention may be obtained by the union of the above-mentioned monomer, and it has a number average molecular weight of less than 10,000 as measured in accordance with the gel permeation chromatography method in which the Model 2000 chromatograph apparatus manufactured and sold by Waters Associates Co., U.S.A. is employed. The polymer to be employed in the present invention may also be obtained by the union of the above-mentioned monomer, and suitable examples of the polymer has been set forth hereinbefore. The polymer has a number average molecular weight of 10,000 or more as measured in accordance with the above method.

The monomer, oligomer or polymer may be dissolved or uniformly dispersed in a diluent to prepare a homogeneous liquid mixture. The use of the monomer, as compared to the oligomer or polymer, is preferred because it has generally a high solubility in the diluent so that preparation of a homogeneous liquid mixture can be facilitated. However, the resulting homogeneous liquid mixture, whether it has been prepared from a monomer or from an oligomer or a polymer, can be equally subjected to the subsequent steps, i.e. incorporation of the mixture into the pores of the inorganic porous material, heating or exposing to actinic rays and removal of the diluent, as described later to produce the composite porous material of the present invention.

Examples of the crosslinking agent to be used with a monomer, an oligomer or a polymer include divinylbenzene, divinyltoluene, divinylxylene, divinylnaphthalene, divinylethylbenzene, divinylphenanthrene, trivinylbenzene, divinyldiphenyl, divinyldiphenylmethane, divinyldibenzyl, divinylphenyl ether, divinyldiphenyl sulfide, divinyldiphenylamine, divinyl sulfone, divinyl ketone, divinylfuran, divinylpyridine, divinylquinoline, di(vinylpyridinoethyl)ethylenediamine, diallyl phthalate, diallyl maleate, diallyl fumarate, diallyl succinate, diallyl carbonate, diallyl oxalate, dially adipate, diallyl sebacate, diallyl tartrate, diallylamine, triallylamine, triallyl phosphate, triallyl tricarballylate, triallyl aconitate, triallyl citrate, N,N'-ethylenediacrylamide, N,N'-methylenediacrylamide, N,N'-methylenedimethacrylamide, ethylene glycol dimethacrylate, triethylene glycol dimethacrylate, polyethylene glycol dimethacrylate, trimethylolpropane trimethacrylate, pentaerythritol tetramethacrylate, 1,3-butylene glycol diacrylate, 1,6-hexanediol diacrylate, trimethylpropane triacrylate, pentaerythritol tetraacrylate, triallyl isocyanurate, 1,3,5-triacryloylhexahydro-1,3,5-triazine, diallylmelamine, formaldehyde, acetaldehyde 1,3-divinylpropane, polyalcohol, α,ω-dihalogenoalkane, polyamine, polyepoxide, diisocyanate, sulfur, alkylperoxide, polyaziridine, acid-formaldehyde, dicarboxylic acid and the like.

As the diluent, there may be employed those which are capable of forming a homogeneous liquid mixture with the monomer, oligomer or polymer and the crosslinking agent. For instance, when the monomer, oligomer or polymer is lipophilic, an organic liquid may be advantageously employed as the diluent. On the other hand, when the monomer, oligomer or polymer is hydrophilic, water or an aqueous solution is preferred as the diluent. They may be used alone or mixture.

As will be described later, after the introduction of the homogeneous liquid mixture into the pores of the inorganic porous material, the inorganic porous material containing the homogeneous liquid mixture is heated or exposed to actinic rays to effect polymerization and/or crosslinking reaction of the monomer, oligomer or polymer. In general, for performing the polymerization and/or crosslinking reaction, the inorganic porous material having the homogeneous liquid mixture contained therein is immediately heated or exposed to actinic rays or first dispersed in a dispersion medium and then heated or exposed to actinic rays. In the case of effecting the heating or exposure to actinic rays without dispersing the inorganic porous material in a dispersion medium, the kind of the diluent is not restricted as far as it is capable of forming a homogeneous liquid mixture with the monomer, oligomer or polymer and the crosslinking agent. However, in the case of effecting the heating or exposure to actinic rays after dispersing the inorganic porous material in a dispersion medium, the diluent should be selected taking into consideration the property of the dispersion medium. That is, when the dispersion medium is hydrophilic, a lipophilic organic liquid is preferred as the diluent. When the dispersion medium is lipophilic, a hydrophilic liquid is preferred as the diluent.

In the process of the present invention, the micro-void characteristics of the organic resin contained in the pores of the inorganic porous material depend on the kind and/or amount of the diluent. For example, the diameter of the micro-voids of the organic resin depends on the affinity of the diluent for a crosslinked polymer to be formed, that is, the lower the affinity, the larger the diameter of the micro-void. Further, the micro-void volume of the organic resin depends on the amount of the diluent to be used, that is, the larger the amount of the diluent, the larger the micro-void volume. As will be described later, a functional group may be introduced into the organic resin of the composite porous material by post-reaction. For example, a sulfonic acid group is introduced, by post-reaction, into a styrene-divinylbenzene copolymer as the organic resin contained in a composite porous material to convert the organic resin to have a capacity of ion exchange. In case such introduction of a functional group is intended, it is preferable that the diluent be used in such an amount as will give not only a micro-void volume sufficient for the post-reaction to an organic resin to be formed from a homogeneous liquid mixture containing the diluent but also a micro-void volume sufficient for the purpose to the organic resin of an ultimate composite porous material.

Specific examples of the diluent to be used in the present invention include water and organic liquids such as chlorobenzene, toluene, xylene, decane, octane, butanol, octanol, diethyl phthalate, dioctyl phthalate, ethyl benzoate, methyl isobutyl ketone, ethyl acetate, diethyl oxalate, ethyl carbonate, nitroethane and cyclohexanone.

The prepared homogeneous liquid mixture is then contacted with an inorganic porous material to introduce the mixture into the pores of the inorganic porous material. Various methods can be employed for introducing into the pores of the particulate inorganic porous material the homogeneous liquid mixture. For example, there may be mentioned a method in which the particulate inorganic porous material is simply contacted with the homogeneous liquid mixture under atmospheric pressure, preferably while effecting gentle agitation, a method in which the particulate inorganic porous material is contacted with the homogeneous liquid mixture under vacuum and a method in which a surface treatment such as silylation is effected on the particulate inorganic porous material and then the thus treated inorganic porous material is contacted with the homogeneous liquid mixture.

When the surface treatment of the inorganic porous material is effected by silylation, a silylating agent to be used is chosen taking into consideration the property of a homogeneous liquid mixture to be introduced. For example, in the case wherein a homogenous liquid mixture is lipophilic, trimethylchlorosilane, vinyltrimethoxysilane, vinyltriethoxysilane, phenyltrichlorosilane and the like are preferred as a silytating agent. On the other hand, in the case where a homogeneous liquid mixture is hydrophilic, γ-glycidoxypropyltrimethoxysilane, γ-(2-aminoethyl)aminopropyltrimethoxysilane, vinyltriacetoxysilane, vinyltrimethoxysilane and the like may be preferably employed as a silylating agent.

With respect to the method of silylation, there is no special limitation, but it is preferred that a silylating agent be contacted with an inorganic porous material in a state of liquid or gas so that the entire inner wall surface of the pores of the inorganic porous material is sufficiently treated with the silylating agent. Therefore, if a solid silylating agent is employed, it is preferably used in the form of a solution or dispersion thereof in an organic liquid or water. The silylating agent may be used in an amount of 0.1 to 20 %, preferably 0.5 to 10%, based on the weight of the inorganic porous material. Silylation reaction may be effected at a temperature in the range of 10° to 300° C., preferably in the range of 15° to 200 ° C., for a period of 0.5 to 48 hours, preferably for 1 to 24 hours.

As preferred silylating agents, there may be mentioned, for example, dimethyldichlorosilane, trimethylchlorosilane, phenyltrichlorosilane, diphenyldichlorosilane, methyltrimethoxysilane, dimethyldimethoxysilane, trimethylmethoxysilane, hexamethyldisilazane, N-trimethylsilyl acetamide, γ-mercaptopropyltrimethoxysilane, vinyltrichlorosilane, vinyltriethoxysilane, vinyltrimethoxysilane, vinyltris(β-methoxyethoxy)silane, γ-methacryloxypropyltrimethoxysilane, γ-methacryloxypropyltris(β-methoxyethoxy)silane, β-(3,4-epoxycyclohexyl)ethyltrimethoxysilane, γ-glycidoxypropyltrimethoxysilane, γ-glycidoxypropyltrimethoxysilane, vinyltriacetoxysilane, γ-aminopropyltriethoxysilane, N-β-(aminoethyl)-γ-aminopropyltrimethoxysilane, γ-chloropropyltrimethoxysilane, silyl peroxide and the like.

The thus obtained particulate inorganic porous material containing a homogeneous liquid mixture in its pores often tends to have, on its outer surface, disadvantageously, the homogeneous liquid mixture. In order to prevent the homogeneous liquid mixture from remaining on the outer surface of the inorganic porous material, there may, for example, be used a method in which the amount of the homogeneous liquid mixture to be contacted with the particulate inorganic porous material is previously adjusted to a level which is equal to or less than the pore volume of the particulate inorganic porous material and the introduction is carried out while stirring at a low rate.

On the other hand, the homogeneous liquid mixture present on the outer surface may preferably be removed so that the above-mentioned outer resin volume ratio of the ultimate composite porous material is as small as possible before the polymerization and/or crosslinking reaction of the monomer, oligomer or polymer is initiated. The liquid mixture which has already been present on the outer surface of the inorganic porous material may be removed by, for example, filtration, preferably pressure filtration or centrifugal filtration which enables the period required for the filtration to be reduced. Alternatively, the homogeneous liquid mixture remaining on the outer surface of the inorganic porous material may be removed by a method in which after completion of the introduction of the liquid mixture, the particulate inorganic porous material is dispersed in a medium which does neither react with the liquid mixture nor is soluble in the liquid mixture, followed by forced stirring. In this case, there may preferably be employed a dispersion medium containing a dispersing agent. A dispersing agent has an effect of stably holding in the dispersion medium the liquid mixture detached by forced stirring from the outer surface of the particulate inorganic porous material, so that the detached liquid mixture is prevented from adhering to the outer surface again.

In the above-mentioned method of detaching the homogeneous liquid mixture remaining on the outer surface of the inorganic porous material using a dispersion medium containing a dispersing agent, when water is used as the dispersion medium, the dispersing agent may be a mucilage such as gum arabic, rosin, pectin, alginate, tragacanth gum, agar, methyl cellulose, starch, carboxymethyl cellulose, karaya gum, gelatin and the like; a synthetic polymer such as sodium polyacrylate, polyvinyl alcohol, polyvinyl pyrrolidone, carbopol, diacetoolein and the like; and an inorganic substance such as magnesium, aluminum silicate, berma gel, hydrated magnesium silicate, titanium oxide, zinc oxide, calcium carbonate, talc, barium sulfate, calcium phosphate, aluminum hydroxide, silica acid anhydride and the like. In addition, there may preferably be added a salt such as sodium chloride, a pH controlling agent and a surfactant according to need. With respect to the forced stirring for removing the homogeneous liquid mixture from the outer surface of the inorganic porous material, the lower limit of the rate of stirring is a minimum rate necessary for detaching the liquid mixture from the outer surface of the particulate inorganic porous material, and the upper limit is a maximum rate at which the particulate inorganic porous material remains unbroken. A preferred rate of stirring is 1500 rpm or more. Under agitation at a suitable rate, preferably near the upper limit, the detached liquid mixture can be reduced into particles having a diameter smaller than that of the particulate inorganic porous material. The smaller the particle size of the detached liquid mixture, the easier the detached liquid mixture can be removed by filtration or the like. Alternatively, by choosing the kind of, and controlling the amount of the dispersing agent to be added in the dispersion medium, the liquid mixture in the dispersion medium can be reduced into particles having a diameter smaller than that of the particulate inorganic porous material. After the detachment of the homogeneous liquid mixture, the homogeneous liquid mixture may be separated by filtration or the like. The separation of the homogeneous liquid mixture may be effected immediately after the forced stirring or after the subsequent heating or exposure to actinic rays as will be mentioned later.

According to a further alternative method of detaching from the inorganic porous material the liquid mixture remaining on the outer surface thereof, the inorganic porous material having the liquid mixture on its outer surface is put on a glass filter or the like, and the liquid mixture is washed away by passing through the material an inert liquid which is immiscible with the liquid mixture. The kind of the inert liquid to be used may be varied depending on the kind of the liquid mixture to be used. For example, when the liquid mixture is lipophilic, water is used as the inert liquid.

In the process of the present invention, the homogeneous liquid mixture introduced into the pores of the inorganic porous material is heated or exposed to actinic rays such as light or radiation. Where the homogeneous liquid mixture is of a monomer or oligomer, a crosslinking agent and a diluent, it undergoes polymerization and crosslinking by the heating or exposure to actinic rays. In this case, a radical polymerization initiator or an ionic polymerization initiator may be or may not be previously added to the homogeneous liquid mixture. Generally, however, from the viewpoints of effecting the polymerization at a lower temperature and completing the polymerization within a decreased period of time, it is preferred that a radical polymerization initiator or an ionic polymerization initiator be added. Of such initiators, a radical polymerization initiator is preferred. As the preferred radical polymerization initiator, there may be mentioned, for example, acyl peroxides such as benzoyl peroxide, lauroyl peroxide and the like; azonitriles such as azobisisobutyronitrile and 2,2'-azobis(2,4-dimethylmaleronitrile) and the like; peroxides such as ditertiarybutyl peroxide, dicumyl peroxide, methyl ethyl ketone peroxide and the like; and hydroperoxides such as cumene hydroperoxide, tertiary hydroperoxide and the like. The amount of the initiator to be used depends on the reaction temperature and the amount and kind of the monomer or oligomer, but generally is in the range of from 0.01 to 12% relative to the weight of the monomer or oligomer. In the case where a mixture of a polymer, a crosslinking agent and a diluent is used as the homogeneous liquid mixture and subjected to heating or exposure to actinic rays, the addition of a polymerization initiator is not necessary.

The above-mentioned heating for effecting polymerization and/or crosslinking reaction of the homogeneous liquid mixture may be carried out as it is or in an appropriate dispersion medium at a temperature of 40° to 150° C for 2 to 100 hours. In the case where the polymerization and/or crosslinking reaction is effected as it is, it is preferred that polymerization and/or crosslinking reaction be conducted while stirring at a low rate to prevent the particulate inorganic porous materials from adhering each other due to the resin being formed on the outer surface of the material. In case the polymerization and/or crosslinking reaction is effected in an appropriate dispersion medium, a diluent to be used in the homogeneous liquid mixture should be chosen so that the homogeneous liquid mixture which has been introduced into the pores of the inorganic porous material does not come out into the dispersion medium. To prevent the homogeneous liquid mixture from flowing out of the pores of the particulate inorganic porous material into the dispersion medium, moreover, it is preferred that a particulate inorganic porous material for which surface treatment has been effected using a silylating agent as described hereinbefore or the like be employed.

The composite material which has been produced under the above-mentioned conditions contains therein a diluent. The diluent is effectively removed from the crosslinked polymer in the pores of the inorganic porous material, for example, by a method in which the composite material is immersed in a solvent capable of dissolving the diluent, allowed to stand for an appropriate period of time and subjected to filtration, or by a method in which the composite material is packed in a column and a solvent mentioned above is passed through the column. When an organic liquid is employed as the diluent, the removal of the diluent can be easily attained by using a water-soluble solvent such as methanol and acetone and further washing away the solvent with water.

The thus obtained composite porous material may be useful as it is for practical applications, for example, as an ion exchange resin, a packing material for chromatography, an adsorbent and the like, or may be subjected to a post-reaction to introduce a functional group into the resin in the pores of the inorganic porous material. That is, a composite porous material prepared by using a monomer such as vinylpyridine or vinylimidazol which itself has an ion-exchange property can exhibit an ion exchanging ability without undergoing any post-reaction. On the other hand, a composite porous material prepared by using a monomer such as styrene, as such, does not exhibit an ion exchanging ability. Hence, the thus obtained composite porous material may be subjected to a post-reaction with a functional group-introducing agent such as chlorosulfonic acid, sulfuric acid, anhydrous sulfuric acid or the like to produce a cation exchange resin-containing composite porous material. Alternatively, the composite porous material having no ion exchanging ability is treated with, for example, chloromethyl ether to effect chloromethylation of the resin and then reacted with a secondary or tertiary amine in order to obtain an anion exchange resin-containing composite porous material.

A chelate resin-containing composite material can be obtained by effecting polymerization or copolymerization of a monomer or monomers having a chelate-forming group within the pores of an inorganic porous material. Illustratively stated, a homogeneous liquid mixture of a monomer having a chelate-forming group, a crosslinking agent and a diluent is introduced into the pores of a particulate inorganic porous material, and heated or exposed to actinic rays so that polymerization such as addition polymerization, polycondensation, polyaddition, addition condensation and elimination polymerization of the monomer or monomers is effected, to obtain a chelate resin-containing composite material. For example, when a homogeneous liquid mixture containing formaldehyde and an aromatic compound having a phenolic OH or an amino group is used, addition condensation occurs to obtain a chelate resin-containing composite material. Such a composite porous material prepared by using a monomer having a chelate ligand may, as such, be useful as a chelate resin-containing composite porous material. Examples of the chelate ligand include an alcohol, a phenol, carboxylic acid, an aldehyde, an amide, an ester, an oxide, an amine, a thioether, a thiophenol, an arylphosphine, an arylarsin and the like. On the other hand, a resin such as polystyrene, polyvinylchloride, three-dimensional polymers such as a phenolic resin, a melamine resin or the like, polysaccharides such as cellulose or the like has no chelate ligand. Therefore, a composite porous material containing such a resin having no chelate ligand may be subjected to, for example, chloromethylation and then reacted with a functional group-introducing agent such as iminodiacetic acid, iminodiacetic acid ethyl ester, diethylenetriamine, chloroacetic acid or the like to produce a chelate resin-containing composite porous material.

In introducing a functional group such as an ion exchange group or a chelate ligand into the resin to form an ion exchange resin or a chelate resin, the functional group can be easily introduced into the resin because the present composite porous material has micro-voids within the resin.

As described, according to the present invention, there is provided a composite porous material having a high mechanical strength and dimensional stability while exhibiting a high adsorbing and separating capacity comparable to those of the conventional porous functional resins, due to the unique composite structure composed of an inorganic porous material and, contained in the pores of the inorganic porous material, an organic resin having micro-voids.

According to a further aspect of the present invention, there is provided a process for the separation of a metallic element from a solution containing the same which comprises the steps of:

(1) in either order, (a) packing a column with a solid adsorbent; and (b) treating the adsorbent with an aqueous solution containing an activator, to obtain a column of an activated adsorbent; and (2) passing through the column of the activated adsorbent an aqueous solution containing a metallic element to adsorb the metallic element on the activated adsorbent, thereby separating the metallic element from the solution containing the same, characterized in that as the solid adsorbent, use is made of a composite porous material comprising a particulate inorganic porous material and, contained in the pores of said inorganic porous material, an organic resin having a micro-void, said organic resin being an ion exchange resin or a chelate resin.

When the composite porous material of the present invention is used as a packing material for an adsorption process, liquid chromatography or the like, the flow rate of a developer may be preferably 0.1 cc/cm$^2$·min or more. In order to avoid a pressure loss at a high flow rate of a developer, the flow rate may preferably be 1 to 500 cc/cm$^2$·min, more preferably 10 to 500 cc/cm$^2$·min.

The composite porous material according to the present invention exhibits a mechanical strength that is superior to that of the customary functional resins, while exhibiting high separating and adsorbing capacities comparable to the functional resins. Hence, the composite porous material of the present invention has a wide variety of uses, for example, as a packing material for gas chromatography and liquid chromatography; an adsorbent for acid gases such as hydrogen sulfide, sulfur dioxide, mercaptans, fatty acids and the like, basic gases such as ammonia, amines and the like, and other smelly substances; an adsorbent for heavy metal ions, surfactants, organic compounds, colored substances and polymers in water; and ion exchanger; and a carrier for insolubilized enzymes. When the composite porous material is used as a packing material in liquid chromatography, the separation and purification of a variety of metals such as rare earth elements, thorium, hafnium, rhenium, uranium, gold and the like and isotopes thereof can be effectively performed.

REFERENCE EXAMPLE

A solution obtained by dissolving 50 g of potassium chloride, 32 g of calcium chloride dihydrate and 2 ml of concentrated hydrochloric acid in 120 ml of distilled water was added to 120 g of Snowtex-30 (trade name of a silica sol produced and sold by Nissan Kagaku Kogyo K.K., Japan). The resulting colloid solution was granulated by a spray drier to obtain 106 g of spherical particles having an average particle diameter of 100 $\mu$m. These particles were sintered at 750° C. for 2 hours.

The sintered particles were treated with a 10-fold volume of a 1 N aqueous hydrochloric acid solution at 80° C. for an hour, and then throughly washed with water. Further, they were filtered off and dried to obtain 33.5 g of porous silica gel particles. The average pore diameter of the particles was 120 nm and their pore volume was 0.85 ml/g. The particles had a pore volume ratio of 0.65 and a specific surface area of 28.3 m$^2$/g. It was found from an elementary analysis that the obtained porous silica gel had a composition of SiO$_2$: 98.7 %, KCl: 0.6 %, and CaCl$_2$: 0.7 %.

EXAMPLE 1

10 g of the porous silica particles which were obtained in the Reference Example was put in a 300 ml beaker, and then a solution obtained by mixing 6.4 g of 4-vinylpyridine, 3.6 g of divinylbenzene (56 % purity; a 7:3 mixture of meta and para isomers containing 44 % of vinylethylbenzene as an impurity), 18 g of dioctylphthalate, and 0.1 g of azobisisobutyronitrile was added to the particles. The resulting suspension was agitated at room temperature for 1 hour, and then filtered on a glass filter. The obtained monomer-containing particles were put in a 100 ml flask under a nitrogen gas atmosphere, and heated, under agitation, in an oil bath at 90° C. for 10 hours to effect polymerization of the monomers. After cooling, the produced particulate composite material was taken out and thoroughly washed with ethanol to remove any remaining organic liquid. As a result of the measurement of the pore diameter distribution by a mercury porosimeter using the sufficiently dried sample, it was found that the average pore diameter of the product was 44 nm. The pore volume, specific surface area and micro-void volume ratio of the product were 0.43 ml/g, 39.1 m$^2$/g and 0.64, respectively. Furthermore, the apparent specific gravity of the produced composite material was 0.98, and its exchange capacity was 1.40 meq/g. The composite material exhibited a $\mu$ value of 0.06.

EXAMPLE 2

10 g of spherical porous silica particles having an average pore diameter of 400 nm, a pore volume of 1.05 ml/g, a specific surface area of 10.5 m²/g and an average particle diameter of 80 $\mu$m were put into a 300 ml flask equipped with a magnetic stirrer, and reduced in pressure by a vacuum pump. Next, a homogeneous liquid mixture composed of 6.1 g of styrene and 2.2 g of divinylbenzene (of the same kind as that used in Example 1) as monomers and 0.1 g of benzoyl peroxide was introduced into the flask, together with 12.5 g of ethylbenzene as a diluent in test (1) and without the diluent in test (2), and slowly agitated under reduced pressure at 10° C. for 30 minutes. The resulting mixture was filtered on a glass filter, and washed with water to recover the monomer-containing particles. The particles were heated while slowly agitating in a nitrogen atmosphere at 85° C. for 20 hours to effect polymerization of the monomers.

The reaction product was thoroughly washed with acetone to remove any remaining organic liquid. The porosity of the products was measured by a porosimeter using each of the samples which were sufficiently dried (see Table 1). Furthermore, 5 g of the thoroughly dried composite material was put into a 100 ml reaction flask, and then 30 ml of dichloroethane was added to the flask and agitated at 40° C. for 2 hours, followed by dropwise addition of 20 g of chlorosulfonic acid. The reaction was continued at 40° C. for 2 hours, and the reaction mixture was thrown into an ice water. The solid product was filtered off, and then subjected to steam distillation to remove dichloroethane. The thus obtained reaction product was thoroughly dried, and subjected to porosity measurement by a prosimeter and to measurement of the exchange capacity (cation) (see Table 1).

TABLE 1

|  | Composite material | | Measurement after sulfonation | | |
| --- | --- | --- | --- | --- | --- |
|  | Average pore diameter (nm) | Pore volume (ml/g) | Average pore diameter (nm) | Pore volume (ml/g) | Exchange capacity (meq/g) |
| Test 1 | 26 | 0.56 | 14 | 0.43 | 1.75 |
| Test 2 | — | — | — | — | 0.17 |

Note:
The line (—) shows that no significant value was obtained.

The ultimate composite material in the test (1) had a specific surface area of 86.2 m²/g, a micro-void volume ratio of 0.61 and a $\mu$ value of 0.05.

EXAMPLE 3

280 g of spherical porous silica particles having an average pore diameter of 800 nm, an average particle diameter of 60 $\mu$m, a pore volume of 0.85 ml/g and a specific surface area of 4.3 m²/g were put into a 1 l vessel equipped with a stirrer. The vessel was deaerated by a vacuum pump, and then returned to the atmospheric pressure by introducing nitrogen. Next, a solution obtained by mixing 65 g of chloromethylstyrene (92 % purity, m/p=6/4), 7 g of m-divinylbenzene, 0.7 g of azobisisobutyronitrile, 70 g of xylene and 70 g of n-buthanol was introduced into the vessel, and slowly agitated in a nitrogen atmosphere at room temperature for 2 hours. The mixture was heated at 90° C. for 18 hours. The reaction product was thoroughly washed with methanol. To the product were added 1.5 l of acetone and 50 g of dimethylamine, and reaction was effected at 50° C. for 5 hours. The final reaction product was thoroughly washed with water, 1 N hydrochloric acid and acetone in this order.

The exchange capacity of the thus produced composite material was 1.03 meq/g, and the $\mu$ value was 0.01.

Furthermore, the pore diameter distribution of the thoroughly dried composite material was measured by a porosimeter. As a result, it was found that the product had an average pore diameter of 55 nm, a pore volume of 0.46 ml/g, a specific surface area of 33.5 m²/g and a micro-void volume ratio of 0.73.

Each of the thus obtained composite material and commercially available Dowex ® MSA-1 (trade name of an ion exchange resin manufactured and sold by The Dow Chemical Company, USA) was separately packed in a cylindrical column of 10 cm in diameter up to 10 cm in height. Then, a pressure of 5 kg/cm² was applied from the top to examine a change of height. The height of Dowex ® MSA-1 decreased to 8.9 cm, whereas with respect to the composite material no decrease in height was observed.

EXAMPLE 4

30 g of the composite containing a crosslinked polymer of chloromethylstyrene which was obtained according to the procedures of Example 3 was reacted with 22.0 g of ethyl iminodiacetate in 100 ml of n-butanol at 100° C. for 20 hours. The product was thoroughly washed with methanol to remove the residual ethyl iminodiacetate, followed by reaction with 1 N hydrochloric acid at 80° C. for 5 hours. The mixture was filtered, and the collected particles were washed with water and 1 N hydrochloric acid in sequence. The weight of the particles was 11.1 g after drying. The anion exchange capacity of the composite material was 0.92 meq/g. The product had an average pore diameter of 36 nm, a pore volume of 0.32 ml/g, a specific surface area of 35.6 m²/g and a $\mu$ value of 0.01.

EXAMPLE 5

15 g of a porous glass having an average pore diameter of 80 nm, a maximum particle diameter in the range of 200 $\mu$m to 300 $\mu$m, a pore volume of 1.0 ml/g and a specific surface area of 50 m²/g was thoroughly washed with concentrated nitric acid, and then poured into 20 g of dichloromethylsilane. The mixture was subjected to reaction in a nitrogen atmosphere at room temperature for 15 hours. The product was filtered off, thoroughly washed with anhydrous methanol, and then dried under reduced pressure.

On the other hand, a solution was prepared by mixing 20.0 g of styrene, 5.0 g of divinylbenzene (same as that used in Example 1), 0.22 g of azobisisobutyronitrile and 30 g of ethylbenzene. The solution was mixed with the above dried product, and then filtered on a glass filter. The obtained substance was dispersed in 500 ml of water, and subjected to forced agitation at 1000 rpm for 1 minute, followed by reaction at 90° C. for 15 hours. The reaction product was thoroughly washed with anhydrous methanol and dried under reduced pressure. 10 g of the product was put into a 100 ml three-necked flask, followed by addition of 30 ml of dichloroethane. Then, 20 g of chlorosulfonic acid was dropwise added while agitating at 40° C. The reaction was continued at 40° C.

for 2 hours, and the reaction mixture was poured into water, filtered off, and washed with water to obtain a porous composite material. The product had a cation exchange capacity of 1.47 meq/g, an average pore diameter of 18 nm, a pore volume of 0.40 ml/g, and a specific surface area of 88.9 m$^2$/g. The outer resin volume ratio ($\mu$) of the product was found to be 0.05 as a result of the measurement.

EXAMPLE 6

A composite material containing a cation exchange resin was obtained by carrying out substantially the same operations as described in Example 5, except that 15 g of porous silica particles (specific surface area 16.0 m$^2$/g) having an average pore diameter of 100 nm, a pore volume of 1.0 ml/g, and an average particle diameter of 250 $\mu$m was used in place of the porous glass. The composite material had an exchange volume of 1.62 meq/g, and exhibited a $\mu$ value of 0.01.

When the composite material was examined by a scanning electron microscope, there was little resin adhering to the external surface. The composite material had an average pore diameter of 18 nm, a pore volume of 0.41 ml/g and a specific surface area of 91.1 m$^2$/g.

EXAMPLE 7

100 g of spherical porous silica particles having an average particle diameter of 50 $\mu$m, an average pore diameter of 650 nm and a pore volume of 1.3 ml/g was put into a 300 ml vessel equipped with an electromagnetic stirrer. The vessel was deaerated, and in the vessel gaseous nitrogen was charged to create a nitrogen atmosphere. A mixture composed of 33 g of formylstyrene, 3.0 g of divinylbenzene (95 % purity), 0.5 g of benzoyl peroxide, 70 g of 1,1,2-trichloroethane and 45 g of tetralin was added to the vessel, and slowly agitated under a nitrogen atmosphere for 30 minutes to introduce the mixture into the particles. The temperature was raised to 85° C. and polymerization was carried out while gently agitating at 85° C. for 12 hours. 500 ml of methanol was added to the reaction mixture and further agitated for 30 minutes, followed by filtration of the mixture. The weight of the composite material obtained after drying was 131 g. As a result of the measurement of the pore diameter distribution by a porosimeter, the composite material was found to have an average pore diameter of 42 nm, a pore volume of 0.68 ml/g, a specific surface area of 64.8 m$^2$/g, and a micro-void volume ratio of 0.75. An infrared spectrum (using KBr tablet) showed a strong absorption of —CHO at 1,720 cm$^{-1}$.

EXAMPLE 8

20 g of the composite material obtained in Example 7 was added to a solution composed of 100 g of dimethylformamide and 4 g of o-phenylenediamine in a 500 ml flask. The mixture was heated up to 80° C. while introducing sulfur dioxide gas and agitated for 5 hours in this state. The total amount of sulfur dioxide gas introduced was 2.5 g. After addition of 300 ml of methanol, the mixture was filtered and washed with water to remove the solvent. The recovered particles were soaked in 1 N hydrochloric acid, again filtered, and washed with methanol. The weight of the composite material particles after drying was 22.3 g. The product had an anion exchange capacity of 1.47 meq/g, an average pore diameter of 41 nm, a pore volume of 0.59 ml/g and a specific surface area of 56.7 m$^2$/g.

EXAMPLE 9

100 g of porous silica gel having an average pore diamter of 150 nm, a pore volume ratio of 0.70, a specific surface area of 28.3 m$^2$/g and a particle diameter in the range of 100 to 500 $\mu$m was put into a 1 l flask. An aqueous solution was separately prepared by dissolving 180 g of catechol and 130 g of formalin (37 % aqueous formaldehyde solution) in 150 g of 20 % sulfuric acid. The aqueous sulfuric acid solution was poured into the flask thereby to soak the porous silica gel in the solution, followed by deaeration for 30 seconds under a reduced pressure of 10 mmHg or less. The wet silica gel obtained by filtering the mixture was put into a separately provided 3 l three-necked flask, and 1.5 l of 1,2,3-trichloropropane was poured thereinto. A reflux condenser, a thermometer and a stirrer were attached to the three-necked flask, and the mixture was subjected to forced agitation at 3,000 rpm for 1 minute. Then, the mixture was heated up to 90° C. while agitating at 100 rpm, and the heating under agitation was continued for 15 hours. After cooling, the product was collected by filtration, and washed with a sufficient amount of water until the water employed for washing became neutral. The product was dried at 80° C. for 12 hours to obtain 276 g of a composite porous material. A differential spectrum from an infrared absorption spectrum (using a KBr tablet) of this composite material and that of the porous silica gel used for the synthesis thereof respectively showed:

1,140–1,290 cm$^{-1}$ (strong and broad; C-O stretching) and 1,360 cm$^{-1}$ (OH angle variation), thereby ensuring that catechol was contained in the composite material. The product had an average pore diameter of 53 nm, a pore volume of 0.48 ml/g and a specific surface area of 36.2 m$^2$/g.

EXAMPLE 10

6 g of a commercially available agarose and 94 g of water were heated up to 60° C. and agitated at the temperature to prepare a homogeneous solution. 20 g of 1,3-dibromopropane and then 60 g of silica gel having an average pore diameter of 150 nm, a pore volume ratio of 0.70 and a particle diameter of 100 to 500 $\mu$m were added to the solution, mixed, and subjected to filtration while heating. The resulting silica gel was put into a flask in which 500 ml of 1,2-dichloroethane was put, heated, subjected to forced agitation at 4,000 rpm for 30 seconds, and heated for 4 hours. After completion of the reaction, the particles were thoroughly washed with acetone and neutralized with 0.01 N caustic soda. The particles were then added to a solution obtained by dissolving 60 g of diethylaminoethyl chloride hydrochloric acid salt in 300 ml of water in a flask, and heated under agitation at 70° C. for 10 hours. The product was thoroughly washed with water and filtered off to obtain 68.3 g of a composite porous material. The product had an average pore diameter of 10 nm, a pore volume of 0.82 ml/g and a specific surface area of 328 m$^2$/g.

EXAMPLE 11

A column, equipped with a jacket made of Pyrex glass, of 20 mm in inside diameter and 1000 mm in height was packed with a composite porous material containing an anion exchange resin to 900 mm in height.

The composite material used in the present example was synthesized as follows:

1 kg of porous silica gel particles having an average pore diameter of 600 nm, a pore volume of 1.05 ml/g, a specific surface area of 7.0 m$^2$/g and an average particle diameter of 500 μm was put into a 5 l flask equipped with a magnetic stirrer, and the pressure was reduced by a vacuum pump. Next, a homogeneous solution composed of 515 g of chloromethylstyrene, 85 g of divinylbenzene, 1.25 kg of methyl benzoate and 1.0 kg of n-heptane was introduced into the flask, and agitated under reduced pressure at 10° C. for 30 minutes. The product was filtered off on a glass filter, dispersed in a solution of 500 g of calcium phosphate in 10 l of water, and subjected to forced agitation at 2,000 rpm for 2 minutes. Then, polymerization was effected under a nitrogen atmosphere at 85° C. for 20 hours. The reaction product was filtered off, and thoroughly washed with water and then with methanol to remove any remaining organic liquids. 500 g of the sufficiently dried composite material was put into a 10 l reaction flask, followed by addition of 3 l of dichloroethane, and agitated at 40° C. for 2 hours. A 20 wt % ethanol solution of trimethylamine was then dropwise added, and heated, for amination, at 40° C. for 5 hours to obtain a composite porous material.

As a result of porosity measurement of the thus obtained particles, which were sufficiently dried, by a porosimeter, it was found that the product had an average pore diameter of 43 nm, a pore volume of 0.64 ml/g, a specific surface area of 59.5 m$^2$/g and an exchange capacity of 1.02 meq/g.

A sufficient amount of 1 N hydrochloric acid was supplied to the column packed with these composite particles to convert the packing material to a chloride ion type. 100 l of a solution containing 100 ppm of chromic acid which was adjusted to a pH value of 5 with hydrochloric acid was fed to the column by a pump. The solution that flowed out from the lower part of the column was fractionated to obtain 500 ml fractions, and the concentration of chromic acid ion was measured with respect to each of the fractions by a fluorescent X-ray analyser. As a result, it was found that the concentration of chromic acid ion in each of the fractions was less than 0.5 ppm, showing a removal ratio of 99.5 % or more. Next, a sufficient amount of an aqueous solution containing 10 wt % NaCl and 1 wt % NaHCO$_3$ was passed through the column to regenerate the packing material. When pressure losses accompanying the feeding of the solution were measured by repeating the operations of adsorption and regeneration 10 times, their change with time was quite small. In addition, a change of height with time of the packing material was also extremely small, ensuring the stable operation of the column (see Table 2).

After repeating the adsorption and regeneration operations 10 times, a portion of the packing material mainly at the lower part of the column was taken out, and the destruction state of the portion was observed by a microscope. Only less than 0.3 % of the portion was recognized as being destroyed.

TABLE 2

| No. of developments repeated | Pressure loss at eluent development (kg/cm$^2$) | Height of packing material (mm) |
| --- | --- | --- |
| 1 | 3.4 | 900 |
| 2 | 3.4 | 900 |
| 3 | 3.4 | 900 |
| 4 | 3.4 | 899 |
| 5 | 3.4 | 899 |
| 6 | 3.5 | 898 |
| 7 | 3.5 | 897 |
| 8 | 3.5 | 897 |
| 9 | 3.5 | 897 |
| 10 | 3.5 | 897 |

COMPARATIVE EXAMPLE 1

For comparison, substantially the same experiment as in Example 11 was carried out by using an anion exchange resin synthesized as follows. That is to say, a 20 l four-necked flask equipped with a stirrer and a thermometer was charged with 20 kg of water, 120 g of sodium polyacrylate as a suspending agent, 240 g of sodium chloride, 1000 g of chloromethylstyrene, 165 g of divinylbenzene, 2.43 kg of methyl benzoate, and 1.94 kg of n-heptane. The mixture was sufficiently agitated to disperse the oil drops. The resulting suspension was subjected to polymerization at 85° C. for 20 hours, and then cooled. The thus obtained resin was transferred into a washing tower equipped with a filter, and thoroughly washed with water and 30 l of methanol in sequence. After washing, the resin was aminated with a 20 wt % ethanol solution of trimethylamine at 40° C. for 5 hours in dichloroethane in substantially the same manner as in the case of the composite material particles of Example 11. The thus obtained resin was thoroughly dried, and subjected to porosity measurement by a porosimeter. The product had an average pore diameter of 58 nm, a more volume of 0.72 ml/g and an exchange capacity of 3.74 meq/g.

Substantially the same adsorption test as described in Example 11 except that this resin was used in place of the composite material particles were carried out thereby to find that the concentration of chromic acid ion in the eluent solution was 0.5 ppm or less and that the removal ratio was 99.5 % or more.

Pressure losses accompanying the feeding of the solution were measured by repeating the operations of adsorption and regeneration 10 times in substantially the same manner as in Example 11. As shown in Table 3, the change of pressure loss with time was fairly large, accompanied by substantial changes in the height of the packing material. Hence, it was difficult to continue safe operations.

After repeating the adsorption and regeneration operations 10 times, a portion of the packing material mainly at the lower part of the column was taken out, and the destruction state of the portion was observed by a microscope. As a result, it was found that 4 % of the portion was recognized as being destroyed.

TABLE 3

| No. of developments repeated | Pressure loss at eluent development (kg/cm$^2$) | Height of packing material (mm) |
| --- | --- | --- |
| 1 | 3.6 | 894 |
| 2 | 4.7 | 873 |
| 3 | 5.9 | 857 |
| 4 | 6.2 | 850 |
| 5 | 8.5 | 847 |
| 6 | 6.9 | 840 |
| 7 | 7.4 | 837 |

TABLE 3-continued

| No. of developments repeated | Pressure loss at eluent development (kg/cm$^2$) | Height of packing material (mm) |
|---|---|---|
| 8 | 7.7 | 832 |
| 9 | 8.3 | 829 |
| 10 | 8.5 | 825 |

EXAMPLE 12

10 g of the porous silica particles obtained in the Reference Example (average pore diameter 120 nm, pore volume 0.85 ml/g, specific surface area 28.3 m$^2$/g) were put into a 100 ml flask, and the pressure within the flask was reduced by a vacuum pump. 2.5 g of styrene, 0.2 g of divinylbenzene and 0.03 g of benzoyl peroxide were charged in the flask to cause the same to be adsorbed to the particles. The mixture was heated up to 85° C. while slowly agitating, and polymerized by heating at that temperature for 10 hours. The product was thoroughly washed with toluene and acetone in this order, and dried at 50° C. under vacuum. The weight of the thus obtained composite material (A) was 13.8 g, and its specific surface area was 10.4 m$^2$/g.

On the other hand, a composite material (B) was obtained by following substantially the same procedures as described above except that the pores of the particles were filled with a mixture of 2.5 g of styrene, 0.2 g of divinylbenzene, 0.03 g of benzoyl peroxide and 5.5 ml of methyl isobuthyl ketone. 14.2 g of a composite material having a surface area of 59.2 m$^2$/g was obtained. The composite material (A) was shown for a comparison, whereas the composite material (B) is of the present invention.

What is claimed is:

1. A composite porous material comprising a particulate inorganic porous material and, contained in the pores of said inorganic porous material, a crosslinked organic resin having a micro-void, said composite material having a surface area larger than that of said inorganic porous material.

2. A composite porous material according to claim 1, wherein said particulate inorganic porous material has an average particle diameter of 10 μm to 1 mm.

3. A composite porous material according to claim 1, wherein said particulate inorganic porous material has a pore volume ratio of 0.3 to 0.9.

4. A composite porous material according to claim 1, wherein said particulate inorganic porous material has an average pore diameter of 20 nm to 2000 nm.

5. A composite porous material according to claim 1, wherein said crosslinked organic resin has a micro-void volume ratio of 0.40 to 0.95 as measured in a dry state.

6. A composite porous material according to claim 1, wherein said crosslinked organic resin has an average micro-void diameter not larger than 90 % of the average pore diameter of said particulate inorganic porous material.

7. A composite porous material according to claim 1, wherein said crosslinked organic resin has an average micro-void diameter of 10 nm to 800 nm.

8. A composite porous material according to claim 1, wherein said particulate inorganic porous material is a porous silica particle.

9. A composite porous material according to claim 1, wherein said crosslinked organic resin is an ion exchange resin or a chelate resin.

10. A process for producing a composite porous material, which comprises contacting a particulate inorganic porous material with a homogeneous liquid mixture selected from the group consisting of a mixture of a polymerizable monomer or oligomer, a crosslinking agent and a diluent and a mixture of a polymer, a crosslinking agent and a diluent to introduce said homogeneous liquid mixture into the pores of said particulate inorganic porous material, heating or exposing to actinic rays the mixture to produce an intermediate product comprising said inorganic porous material and, disposed in the pores of said inorganic porous material, a crosslinked polymer containing the diluent and removing the diluent from said intermediate product.

11. A process according to claim 10, wherein said homogeneous liquid mixture is a mixture of a polymerizable monomer, a crosslinking agent and a diluent.

12. A process according to claim 10, which further comprises reacting said crosslinked polymer with a functional group-introducing agent to introduce a functional group into said crosslinked polymer.

13. A process according to claim 10, wherein said homogeneous liquid mixture further contains a radical initiator.

14. A process according to claim 10, wherein said particulate inorganic porous material is porous silica particles.

15. A process according to claim 14, wherein said porous silica particles are those produced from a solution comprising a silica sol.

16. A process according to claim 15, wherein said porous silica particles are those produced by spraying a solution comprising a silica sol into air to form liquid particles and drying said liquid particles.

* * * * *